United States Patent
Yamaguchi et al.

(10) Patent No.: US 11,219,619 B2
(45) Date of Patent: Jan. 11, 2022

(54) THERAPEUTIC AGENT FOR HEPATOCELLULAR CARCINOMA

(71) Applicant: Eisai R&D Management Co., Ltd., Tokyo (JP)

(72) Inventors: Atsumi Yamaguchi, Tsukuba (JP); Hajime Shimizu, Tsukuba (JP); Satoshi Goda, Tsukuba (JP); Saori Miyano, Tsukubamirai (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 16/970,683

(22) PCT Filed: Mar. 26, 2019

(86) PCT No.: PCT/JP2019/012971
§ 371 (c)(1),
(2) Date: Aug. 18, 2020

(87) PCT Pub. No.: WO2019/189241
PCT Pub. Date: Oct. 3, 2019

(65) Prior Publication Data
US 2020/0375970 A1    Dec. 3, 2020

(30) Foreign Application Priority Data
Mar. 28, 2018 (JP) .............................. JP2018-061447

(51) Int. Cl.
*A61K 31/4545* (2006.01)
*A61K 45/06* (2006.01)

(52) U.S. Cl.
CPC .......... *A61K 31/4545* (2013.01); *A61K 45/06* (2013.01)

(58) Field of Classification Search
None
See application file for complete search history.

(56) References Cited

U.S. PATENT DOCUMENTS

| | | |
|---|---|---|
| 6,831,175 B2 | 12/2004 | Li et al. |
| 7,109,219 B2 | 9/2006 | Tsuruoka et al. |
| 7,253,286 B2 | 8/2007 | Funahashi et al. |
| 8,131,527 B1 | 3/2012 | Saxty et al. |
| 8,614,216 B2 | 12/2013 | Okhamafe et al. |
| 8,933,099 B2 | 1/2015 | Funahashi et al. |
| 9,951,047 B2 * | 4/2018 | Ozaki .................. C07C 55/02 |
| 2004/0053908 A1 | 3/2004 | Funahashi et al. |
| 2004/0122029 A1 | 6/2004 | Liu et al. |
| 2004/0204427 A1 | 10/2004 | Chen et al. |
| 2005/0187236 A1 | 8/2005 | Tsuruoka et al. |
| 2005/0256154 A1 | 11/2005 | Luk et al. |
| 2008/0108648 A1 | 5/2008 | Alcouffe et al. |
| 2011/0060215 A1 | 3/2011 | Tupin et al. |
| 2012/0270918 A1 | 10/2012 | Abecassis et al. |
| 2013/0338134 A1 | 12/2013 | Wu et al. |
| 2014/0142084 A1 | 5/2014 | Kameda et al. |
| 2014/0155385 A1 | 6/2014 | Bad et al. |
| 2014/0235614 A1 | 8/2014 | Funasaka et al. |
| 2015/0191791 A1 | 7/2015 | Shibata |
| 2017/0217935 A1 | 8/2017 | Ozaki et al. |
| 2018/0015079 A1 | 1/2018 | Shibata et al. |
| 2018/0303817 A1 | 10/2018 | Miyano et al. |

FOREIGN PATENT DOCUMENTS

| | | |
|---|---|---|
| AU | 2014219811 | 8/2014 |
| CL | 201400130 | 8/2014 |
| CN | 1678607 | 10/2005 |
| CN | 101024627 | 8/2007 |
| CN | 103917545 | 7/2014 |
| EP | 1415987 | 5/2004 |
| EP | 1522540 | 4/2005 |
| EP | 2657233 | 8/2014 |
| JP | 2008-533111 | 3/2006 |
| JP | 2006-522756 | 10/2006 |
| JP | 2009-215313 | 9/2009 |
| JP | 5600229 | 10/2014 |
| JP | 2014-237707 | 12/2014 |
| JP | 2015-505562 | 2/2015 |
| JP | 5925978 | 4/2016 |
| KR | 10-2005-0059151 | 6/2005 |
| RU | 2257380 | 7/2005 |
| RU | 2005108999 | 8/2005 |
| RU | 2345077 | 2/2006 |
| RU | 2310651 | 11/2007 |
| TW | 200413353 | 8/2004 |
| WO | WO 2002/032872 | 4/2002 |
| WO | WO 2004/020434 | 3/2004 |
| WO | WO 2006/000420 | 1/2006 |
| WO | WO 2006/097625 | 9/2006 |
| WO | WO 2007/071752 | 6/2007 |
| WO | WO 2008/008747 | 1/2008 |
| WO | WO 2008/012690 | 1/2008 |
| WO | WO 2008/075068 | 6/2008 |

(Continued)

OTHER PUBLICATIONS

Forner et al., The Lancet (2012), 379, 1245-1255.*
Office Action in Mexican Patent Application No. MX/a/2017/009892, dated Jul. 14, 2020, 7 pages (with English Translation).
Office Action in Mexican Patent Application No. MX/a/2018/006329, dated Jul. 17, 2020, 6 pages (with English Translation).
"Cancer classification, NCI, from internet", 2008, p. 1-p. 3.
Andre et al., "Targeting FGFR with Dovitinib (TKI258): Preclinical and Clinical Data in Breast Cancer", Clinical Cancer Research, vol. 19, No. 13, Jul. 1, 2013, p. 3693-p. 3702.

(Continued)

*Primary Examiner* — Brian J Davis
(74) *Attorney, Agent, or Firm* — Fish & Richardson P.C.

(57) ABSTRACT

Disclosed is a therapeutic agent for hepatocellular carcinoma, comprising 5-((2-(4-(2-hydroxyethyl)piperidin-4-yl)benzamide)pyridin-4-yl)oxy)-6-(2-methoxyethoxy)-N-methyl-1H-indole-1-carboxamide or a pharmacologically acceptable salt thereof.

2 Claims, 1 Drawing Sheet

(56) References Cited

FOREIGN PATENT DOCUMENTS

| | | |
|---|---|---|
| WO | WO 2008/078091 | 7/2008 |
| WO | WO 2008/078100 | 7/2008 |
| WO | WO 2009/001070 | 12/2008 |
| WO | WO 2009/019518 | 2/2009 |
| WO | WO 2009/047506 | 4/2009 |
| WO | WO 2009/047522 | 4/2009 |
| WO | WO 2009/056886 | 5/2009 |
| WO | WO 2009/076602 | 6/2009 |
| WO | WO 2009/141386 | 11/2009 |
| WO | WO 2009/150240 | 12/2009 |
| WO | WO 2009/153592 | 12/2009 |
| WO | WO 2010/078421 | 7/2010 |
| WO | WO 2010/078427 | 7/2010 |
| WO | WO 2010/078430 | 7/2010 |
| WO | WO 2010/119284 | 10/2010 |
| WO | WO 2010/119285 | 10/2010 |
| WO | WO 2011/001122 | 1/2011 |
| WO | WO 2011/001413 | 1/2011 |
| WO | WO 2011/016528 | 2/2011 |
| WO | WO 2011/051425 | 5/2011 |
| WO | WO 2011/071821 | 6/2011 |
| WO | WO 2011/135376 | 11/2011 |
| WO | WO 2012/004732 | 1/2012 |
| WO | WO 2012/073017 | 6/2012 |
| WO | WO 2012/088266 | 6/2012 |
| WO | WO 2013/010380 | 1/2013 |
| WO | WO 2013/061074 | 5/2013 |
| WO | WO 2013/061077 | 5/2013 |
| WO | WO 2013/061080 | 5/2013 |
| WO | WO 2013/061081 | 5/2013 |
| WO | WO 2013/087744 | 6/2013 |
| WO | WO 2013/108809 | 7/2013 |
| WO | WO 2013/116293 | 8/2013 |
| WO | WO 2013/129369 | 9/2013 |
| WO | WO 2013/179034 | 12/2013 |
| WO | WO 2014/007369 | 1/2014 |
| WO | WO 2014/011900 | 1/2014 |
| WO | WO 2014/026125 | 2/2014 |
| WO | WO 2014/044846 | 3/2014 |
| WO | WO 2014/048878 | 3/2014 |
| WO | WO 2014/051022 | 3/2014 |
| WO | WO 2014/129477 | 8/2014 |
| WO | WO 2014/145751 | 9/2014 |
| WO | WO 2014/162039 | 10/2014 |
| WO | WO 2016/027781 | 2/2016 |
| WO | WO 2016/152907 | 9/2016 |
| WO | WO 2017/104739 | 6/2017 |

OTHER PUBLICATIONS

Applicant's unpublished experimental data, 2014, 1 page.
Arai et. al, "Fibroblast Growth Factor Receptor 2 Tyrosine Kinase Fusions Define a Unique Molecular Subtype of Cholangiocarcinoma", Hepatology, 2014, vol. 59, No. 4, p. 1427-p. 1434.
Berrada et al., "Treatment of triple-negative metastatic breast cancer: toward individualized targeted treatments or chemosensitization?," Annals of Oncology, vol. 21, Supplement 7, 2010, p. vii30-p. vii35.
Bono et al., "Inhibition of Tumor Angiogenesis and Growth by a Small-Molecule Multi-FGF Receptor Blocker with Allosteric Properties", Cancer Cell, 2013, p. 477-p. 488.
Borad et al., "Integrated Genomic Characterization Reveals Novel, Therapeutically Relevant Drug Targets in FGFR and EGFR Pathways in Sporadic Intrahepatic Cholangiocarcinoma", PLOS Genetics, 2014, vol. 10, Issue 2, p. 1-p. 21.
Bucci et al., "Circadian Rhythms: channels contribute," Nature Chem Bio., Jun. 2013, 9:349.
Cancer Genome Atlas Research Network, "Comprehensive genomic characterization of squamous cell lung cancers," Nature, 2012, 489(7417):519-525.
Celina Ang, "Role of the fibroblast growth factor receptor axis incholangiocarcinoma", Journal of Gastroenterology and Hepatology, 2015, vol. 30, p. 1116-p. 1122.
Chen et al., "Inhibition of endogenous SPARC enhances pancreatic-cancer cell growth: modulation by FGFR1-III isoform expression", Br J Cancer, 2010(102), p. 188-p. 195.
Choi et al., "Molecular Targeted Therapy for Hepatocellular Carcinoma: Present Status and Future Directions," Biological and Pharmaceutical Bulletin, 2015, 38:986-991.
Daniele et al., "FGF Receptor Inhibitors: Role in Cancer Therapy", Curr Oncol Rep., 2012(14), p. 111-p. 119.
Dey et al., "Targeting Fibroblast Growth Factor Receptors Blocks PI3K/AKT Signaling, Induces Apoptosis, and Impairs Mammary Tumor Outgrowth and Metastasis," Cancer Research, vol. 70, No. 10, May 15, 2010, p. 4151-p. 4162.
European Search Report in European Application No. 14754294.8, dated Jul. 15, 2016, 5 pages.
European Search Report in European Application No. 15834302.0, dated Mar. 15, 2018, 6 pages.
European Search Report in European Application No. 16768810.0, dated Aug. 17, 2018, 7 pages.
European Search Report in European Application No. 16768810.0, dated Dec. 11, 2018, 7 pages.
European Search Report in European Application No. 16875716.9, dated Jul. 29, 2019, 9 pages.
Foulkes et al., "Triple-Negative Breast Cancer," The New England Journal of Medicine, Nov. 11, 2010, 363:1938-1948.
French et al., "Targeting FGFR4 Inhibits Hepatocellular Carcinoma in Preclinical Mouse Models", PLoS One, 2012(7), p. 1-p. 12.
Gavine et al., "AZD4547:An Orally Bioavailable, Potent, and Selective Inhitor of the Fibroblast Growth Factor Receptor Tyrosine Kinase Family", Cancer Res, 2012(72), p. 2045-p. 2056.
Gould, "Salt selection for basic drugs," International Journal of Pharmaceutics, 1986, 33:201-217.
Guagnano et al., "Discovery of 3-(2,6-Dichloro-3,5-dimethoxyphenyl)-1-{6-[4-(4-ethyl-piperazin-1-yl)-phenylamino]-pyrimidin-4-yl}-1-methyl-urea (NVP-BGJ398), A Potent and Selective Inhibitor of the Fibroblast Growth Factor Receptor Family of Receptor Tyrosine Kinase", J Med Chem, 2011(54).
Guagnano et al., "FGFR Genetic Alterations Predict for Sensitivity to NVP-BGJ398, a Selective Pan-FGFR Inhibitor", Cancer Discovery, Sep. 20, 2012, p. 1118-p. 1133.
Harbinski et al., "Rescue Screens with Secreted Proteins Reveal Compensatory Potential of Receptor Tyrosine Kinases in Driving Cancer Growth", Cancer Discovery, Aug. 8, 2012, p. 948-p. 958.
International Preliminary Report on Patentability in International Application No. PCT/JP2014/053819, dated Sep. 3, 2015, 7 pages.
International Preliminary Report on Patentability in International Application No. PCT/JP2015/073047, dated Mar. 2, 2017, 6 pages (English Translation).
International Preliminary Report on Patentability in Patent Application No. PCT/JP2016/059162, dated Oct. 5, 2017, 8 pages (English Translation).
International Preliminary Report on Patentability in Patent Application No. PCT/JP2016/087349, dated Jun. 28, 2018, 9 pages.
International Search Report and Written Opinion in International Application No. PCT/JP2019/012971, dated May 14, 2019, 11 pages (with Partial Translation).
International Search Report for PCT/JP2015/073047 dated Nov. 17, 2015, 2 pages (English translation).
International Search Report in International Application No. PCT/JP2014/053819, dated Apr. 15, 2014, 9 pages.
International Search Report in International Application No. PCT/JP2016/059162, dated May 24, 2016, 2 pages (English Translation).
International Search Report in International Application No. PCT/JP2016/087349, dated Feb. 7, 2017, 2 pages (English Translation).
International Search Report in International Application No. PCT/JP2018/037690, dated Jan. 15, 2019, 7 pages.
Ishiwata et al., "Enhanced Expression of Fibroblast Growth Factor Receptor 2 IIIc Promotes Human Pancreatic Cancer Cell Proliferation", Am J Pathol, 2012(180), p. 1928-p. 1941.

(56) References Cited

OTHER PUBLICATIONS

Kim et al., "Regorafenib in advanced hepatocellular carcinoma (HCC): considerations for treatment," Cancer Chemotherapy and Pharmacology, 2017, 80:945-954.
Koziczak et al., "Blocking of FGFR signaling inhibits breast cancer cell proliferation through downregulation of D-type cyclins", Oncogene, vol. 23, 2004, p. 3501-p. 3508.
Li et al., "Preparation of heteroaryls for therapeutic use in pharmaceutical compositions as kinase inhibitors for treatment of hyperproliferative diseases, including cancer," 2003, CA139:323437.
Llovet et al., "Sorafenib in Advanced Hepatocellular Carcninoma," The New England Journal of Medicine, 2008, 359:378-390.
Logie et al., "Activating mutations of the tyrosine kinase receptor FGFR3 are associated with benign skin tumors in mice and humans", Hum Mol Genet, 2005(14), p. 1153-p. 1160.
Mohammadi et al., "Crystal structure of an angiogenesis inhibitor bound to the FGF receptor tyrosine kinase domain", The EMBO Journal vol. 17 No. 20, 1998, p. 5896-p. 5904.
Nicholas et al., "Fibroblast growth factor signalling:from development to cancer", Nature Reviews Cancer, 2010(10), p. 116-p. 129.
Norman et al., "Protein—Ligand Crystal Structures Can Guide the Design of Selective Inhibitors of the FGFR Tyrosine Kinase", Journal of Medicinal Chemistry, May 21, 2012, p. 5003-p. 5012.
Notice of Allowance in Australian Patent Application No. 2014219811, dated Sep. 13, 2017, 3 pages.
Notice of Allowance in Australian Patent Application No. 2015304465, dated Apr. 24, 2019, 3 pages.
Notice of Allowance in Canadian Patent Application No. 2901585, dated Jun. 5, 2019, 1 page (with English Translation).
Notice of Allowance in Chilean Patent Application No. 2015-02311, dated Dec. 12, 2019, 6 pages (with English Translation).
Notice of Allowance in Chinese Patent Application No. 201480009370.X dated Jul. 25, 2017, 4 pages (English Translation).
Notice of Allowance in Chinese Patent Application No. 201580042132.3, dated Mar. 6, 2019, 4 pages (with English Translation).
Notice of Allowance in European Patent Application No. 14754294.8, dated Jan. 4, 2017, 239 pages.
Notice of Allowance in European Patent Application No. 14754294.8, dated Mar. 9, 2017, 2 pages.
Notice of Allowance in Gulf Cooperation Council Patent Application GCC/P/2014/26467, dated Jan. 7, 2018, 2 pages (English Translation).
Notice of Allowance in Indonesian Patent Application No. P-00201505035, dated Sep. 27, 2019, 4 pages (with English Translation).
Notice of Allowance in Israeli Patent Application No. 240623, dated Jan. 7, 2019, 7 pages (English Translation).
Notice of Allowance in Israeli Patent Application No. 250290, dated Mar. 17, 2020, 10 pages (with English Translation).
Notice of Allowance in Japanese Patent Application No. P2015-560425, dated Apr. 19, 2016, 6 pages (English Translation).
Notice of Allowance in Japanese Patent Application No. P2017-508383, dated Mar. 5, 2019, 6 pages (with English Translation).
Notice of Allowance in Jordanian Patent Application No. 39/2014, dated Apr. 16, 2018, 2 pages (with English Translation).
Notice of Allowance in Korean Patent Application No. 10-2015-7022252, dated Nov. 11, 2019, 5 pages (with English Translation).
Notice of Allowance in Mexican Patent Application No. MX/a/2015/010698, dated Nov. 8, 2018, 4 pages (English Translation).
Notice of Allowance in Mexican Patent Application No. MX/a/2017/001624, dated Oct. 23, 2019, 5 pages (with English Translation).
Notice of Allowance in New Zealand Patent Application No. 711101, dated Jul. 27, 2018, 1 page.
Notice of Allowance in Pakistani Patent Application No. 523/2016, dated Dec. 31, 2019, 3 pages.
Notice of Allowance in Pakistani Patent Application No. 94/2014, dated Dec. 31, 2019, 3 pages.
Notice of Allowance in Russian Patent Application No. 2015134558, dated Jan. 10, 2018, 25 pages (English Translation).
Notice of Allowance in Russian Patent Application No. 2017103439, dated Apr. 10, 2018, 14 pages (English Translation).
Notice of Allowance in Russian Patent Application No. 2017127135, dated Dec. 17, 2019, 16 pages (with English Translation).
Notice of Allowance in Russian Patent Application No. 2018119102, dated Jun. 26, 2020, 12 pages (with English Translation.
Notice of Allowance in Singaporean Patent Application No. 11201506488W, dated Sep. 20, 2017 (English Translation).
Notice of Allowance in Singaporean Patent Application No. 11201700703X, dated Sep. 12, 2017, 5 pages (English Translation).
Notice of Allowance in South African Application No. 2015/05941, dated May 24, 2016, 6 pages.
Notice of Allowance in Taiwanese Application No. 103105419, dated Sep. 11, 2018, 5 pages (English Translation).
Notice of Allowance in Taiwanese Application No. 107134522, dated Jul. 29, 2019, 7 pages (with English Translation).
Notice of Allowance in Taiwanese Application No. 107134526, dated Jul. 29, 2019, 7 pages (with English Translation).
Notice of Allowance in Taiwanese Application No. 107134529, dated Jul. 29, 2019, 7 pages (with English Translation).
Notice of Allowance in Ukrainian Patent Application a201508149, dated Jan. 3, 2018, 16 pages (English Translation).
Notice of Allowance in U.S. Appl. No. 15/500,429, dated Jan. 18, 2018, 6 pages.
Notice of Allowance in U.S. Appl. No. 15/500,429, dated Mar. 29, 2018, 4 pages.
Notice of Allowance in U.S. Appl. No. 14/183,864, dated Nov. 19, 2014, 11 pages.
Notice of Allowance in U.S. Appl. No. 15/500,429, dated Oct. 19, 2017, 11 pages.
Notice of Allowance in U.S. Appl. No. 15/547,139, dated Sep. 28, 2018, 16 pages.
Notice of Allowance in U.S. Appl. No. 15/547,139, dated Mar. 6, 2019, 13 pages.
Notice of Allowance in U.S. Appl. No. 15/547,139, dated Aug. 7, 2019, 17 pages.
Notice of Allowance in U.S. Appl. No. 15/547,139, dated Dec. 5, 2019, 20 pages.
Notice of Allowance in U.S. Appl. No. 15/547,139, dated Dec. 31, 2019, 13 pages.
Notice of Allowance in U.S. Appl. No. 15/547,139, dated Mar. 24, 2020, 23 pages.
Notice of Allowance in U.S. Appl. No. 15/547,139, dated Jun. 23, 2020, 11 pages.
Notice of Allowance in U.S. Appl. No. 16/225,772, dated Oct. 22, 2019, 19 pages.
Notice of Allowance in U.S. Appl. No. 16/225,772, dated Dec. 16, 2019, 9 pages.
Notice of Allowance in U.S. Appl. No. 16/225,772, dated Jan. 15, 2020, 9 pages.
Notice of Allowance in U.S. Appl. No. 16/225,772, dated Apr. 14, 2020, 22 pages.
Notice of Allowance in U.S. Appl. No. 16/225,772, dated Jul. 24, 2020, 10 pages.
Notice of Allowance in Vietnamese Patent Application No. 1-2015-02994, dated Oct. 23, 2017, 2 pages (English Translation).
Office Action in Argentine Patent Application No. P140100495, dated Nov. 11, 2019, 4 pages (with English Translation).
Office Action in Australian Patent Application No. 2014219811, dated Jun. 16, 2017, 2 pages.
Office Action in Australian Patent Application No. 2015304465, dated Jan. 21, 2019, 2 pages.
Office Action in Brazilian Patent Application No. BR112015019790-6, dated Apr. 7, 2020, 14 pages (with English Translation).
Office Action in Canadian Patent Application No. 2901585, dated Jan. 30, 2019, 3 pages.
Office Action in Chilean Patent Application No. 2015-02311, dated Mar. 22, 2017, 21 pages (English Translation).
Office Action in Chilean Patent Application No. 2015-02311, dated Sep. 13, 2017, 13 pages (English Translation).
Office Action in Chinese Application No. 201480009370.X, dated Jan. 9, 2017, 10 pages (English Translation).

(56) References Cited

OTHER PUBLICATIONS

Office Action in Chinese Application No. 201480009370.X, dated May 26, 2016, 7 pages (English Translation).
Office Action in Chinese Patent Application No. 201580042132.3, dated Aug. 8, 2018, 11 pages (English Translation).
Office Action in Chinese Patent Application No. 201680007472.7, dated Jun. 14, 2019, 14 pages (with English Translation).
Office Action in Chinese Patent Application No. 201680007472.7, dated Jan. 15, 2020, 8 pages (with English Translation).
Office Action in Chinese Patent Application No. 201680007472.7, dated May 6, 2020, 8 pages (with English Translation).
Office Action in Chinese Patent Application No. 201680068110.9, dated Mar. 20, 2020, 15 pages (with English Translation).
Office Action in European Patent Application No. 15834302.0, dated Oct. 28, 2019, 4 pages.
Office Action in European Patent Application No. 16768810.0, dated Jun. 18, 2020, 5 pages.
Office Action in Gulf Cooperation Council Patent Application No. GCC/P/2014/26467, dated Jun. 7, 2017, 7 pages (English Translation).
Office Action in Indian Patent Application No. 201747003469, dated Aug. 2, 2019, 5 pages (with English Translation).
Office Action in Indian Patent Application No. 201747027065, dated Jan. 28, 2020, 6 pages (with English Translation).
Office Action in Indian Patent Application No. 201747027065, dated Jul. 8, 2020, 2 pages (with English Translation).
Office Action in Indian Patent Application No. 201847015401, dated May 5, 2020, 7 pages (with English Translation).
Office Action in Indian Patent Application No. 4989/CHENP/2015, dated Jan. 31, 2019, 5 pages (with English Translation).
Office Action in Indonesian Patent Application No. P-00201505035, dated Feb. 1, 2019, 5 pages, (with English Translation).
Office Action in Israeli Application No. 240623, dated Jan. 19, 2016, 5 pages (English Translation).
Office Action in Israeli Patent Application No. 240623, dated Dec. 20, 2017, 8 pages (English Translation).
Office Action in Israeli Patent Application No. 250290, dated Aug. 15, 2019, 8 pages (with English Translation).
Office Action in Israeli Patent Application No. 250290, dated Jan. 29, 2020, 10 pages (with English Translation).
Office Action in Israeli Patent Application No. 250290, dated Sep. 2, 2018, 5 pages (English Translation).
Office Action in Israeli Patent Application No. 253701, dated Nov. 28, 2019, 7 pages (with English Translation).
Office Action in Israeli Patent Application No. 253701, dated Oct. 17, 2018, 7 pages (with English Translation).
Office Action in Israeli Patent Application No. 258671, dated Aug. 4, 2019, 5 page (with English Translation).
Office Action in Israeli Patent Application No. 258671, dated Jun. 25, 2020, 8 pages (with English Translation).
Office Action in Japanese Application No. P2015-560425, dated Mar. 8, 2016, 4 pages (English Translation).
Office Action in Korean Patent Application No. 10-2015-7022252, dated Sep. 5, 2019, 11 pages (with English Translation).
Office Action in Mexican Patent Application No. MX/a/2015/010698, dated Jun. 15, 2018, 9 pages (English Translation).
Office Action in Mexican Patent Application No. MX/a/2017/001624, dated Jun. 25, 2019, 8 pages (with English Translation).
Office Action in New Zealand Patent Application No. 711101, dated May 1, 2018, 2 pages.
Office Action in Pakistani Patent Application No. 523/2016, dated May 3, 2018, 2 pages (English Translation).
Office Action in Pakistani Patent Application No. 94/2014, dated May 3, 2018, 2 pages (English Translation).
Office Action in Pakistani Patent Application No. 94/2014, dated May 13, 2016, 2 pages.
Office Action in Peruvian Patent Application No. 001748-2015, dated Apr. 19, 2019, 19 pages (with English Translation).
Office Action in Russian Patent Application No. 2015134558, dated Aug. 24, 2017, 11 pages (English Translation).
Office Action in Russian Patent Application No. 2015134558, dated Oct. 21, 2015, 3 pages (English Translation).
Office Action in Russian Patent Application No. 2017103439, dated Feb. 6, 2018, 6 pages (English Translation).
Office Action in Russian Patent Application No. 2017127135, dated Aug. 22, 2019, 16 pages (with English Translation).
Office Action in Russian Patent Application No. 2018119102, dated Feb. 4, 2020, 12 pages (with English Translation).
Office Action in Singaporean Patent Application No. 11201700703X, dated Jun. 8, 2017, 5 pages (English Translation).
Office Action in Sri Lankan Patent Application No. 18355, dated Aug. 19, 2019, 1 page.
Office Action in Taiwanese Patent Application No. 103105419, dated May 14, 2018, 4 pages (English Translation).
Office Action in Taiwanese Patent Application No. 103105419, dated Oct. 24, 2017, 7 pages (English Translation).
Office Action in Thai Patent Application No. 1501004679, dated Jun. 11, 2018, 4 pages (English Translation).
Office Action in Thai Patent Application No. 1501004679, dated Sep. 26, 2017, 4 pages (English Translation).
Office Action in Ukrainian Patent Application No. a201508149, dated Aug. 11, 2017, 6 pages (English Translation).
Office Action in Ukrainian Patent Application No. a201508149, dated Oct. 6, 2015, 2 pages (English Translation).
Office Action in U.S. Appl. No. 14/183,864, dated Jun. 4, 2014, 6 pages.
Office Action in U.S. Appl. No. 14/183,864, dated Sep. 16, 2014, 7 pages.
Office Action in U.S. Appl. No. 15/500,429, dated Jul. 31, 2017, 8 pages.
Office Action in U.S. Appl. No. 15/547,139, dated Apr. 30, 2018, 26 pages.
Office Action in U.S. Appl. No. 15/771,193, dated Apr. 1, 2019, 5 pages.
Office Action in U.S. Appl. No. 15/771,193, dated Jun. 7, 2019, 44 pages.
Office Action in U.S. Appl. No. 15/771,193, dated Mar. 24, 2020, 12 pages.
Office Action in U.S. Appl. No. 15/774,193, dated Oct. 16, 2019, 44 pages.
Office Action in U.S. Appl. No. 16/225,722, dated Jul. 9, 2019, 33 pages.
Office Action in Vietnamese Patent Application No. 1-2015-02994, dated Jun. 21, 2017, 2 pages (English Translation).
Office Action in Vietnamese Patent Application No. 1-2015-02994, dated Sep. 30, 2015, 4 pages (English Translation).
Official Notification in Brazilian Patent Application No. BR112015019790-6, dated Jan. 21, 2020, 2 pages (with English Translation).
Official Notification in Brazilian Patent Application No. BR112015019790-6, dated Mar. 10, 2020, 4 pages (with English Translation).
Official Notification in U.S. Appl. No. 15/771,193, dated Aug. 10, 2020, 3 pages.
Patani and LaVoie, "Bioisosterism: A Rational Approach in Drug Design," Chem. Rev., 1996, 96:3147-3176.
Request to Amend Application Before Grant in Singapore Patent Application No. 11201506488W, dated Aug. 3, 2017, 21 pages (English Translation).
Response in Gulf Cooperation Council Patent Application No. GCC/P/2014/26467, dated Aug. 27, 2017, 18 pages (English Translation).
Response in Malaysian Patent Application No. PI2015702696, dated Nov. 6, 2017, 8 pages (English Translation).
Response in U.S. Appl. No. 15/500,429, dated Sep. 27, 2017, 6 pages.
Response in Vietnamese Patent Application No. 1-2015-02994, dated Aug. 7, 2017, 2 pages (English Translation).
Rubini et al., "Synthesis of Isosteric Methylene-Oxy Pseudodipeptide Analogues as Novel Amide Bond Surrogate Units", Tetrahedron, vol. 42, No. 21, 1986, p. 6039-p. 6045.
Sasaki et al., "Increased FGFR1 copy number in lung squamous cell carcinomas", Mol Med Report, 2012(5), p. 725-p. 728.

(56) References Cited

OTHER PUBLICATIONS

Shibata, "Clinical significance of Expression oFGFR2 Fusion Genes in Bile Duct Cancer", The Bilialy Tract & Pancreas, Feb. 12, 2015, vol. 36(2), p. 137-p. 142.
St. Bernard et al., "Fibroblast Growth Factor Receptors as Molecular Targets in Thyroid Carcinoma", Endocrinology, 2005(146), p. 1145-p. 1153.
Submission Document in Argentine Patent Application No. P140100495, dated Jan. 23, 2015, 7 pages (English Translation).
Submission Document in Argentine Patent Application No. P140100495, dated Dec. 17, 2019, 7 pages (with English Translation).
Submission Document in Australian Patent Application No. 2014219811, dated Aug. 22, 2017, 6 pages.
Submission Document in Australian Patent Application No. 2015304465, dated Apr. 5, 2019, 16 pages.
Submission Document in Brazilian Patent Application No. BR112015019790-6, dated Apr. 28, 2016, 19 pages (English Translation).
Submission Document in Brazilian Patent Application No. BR112015019790-6, dated Dec. 22, 2015, 12 pages (English Translation).
Submission Document in Brazilian Patent Application No. BR112015019790-6, dated Dec. 30, 2019, 16 pages (with English Translation).
Submission Document in Brazilian Patent Application No. BR1120170163926, dated Mar. 6, 2019, 16 pages (with English Translation).
Submission Document in Canadian Patent Application No. 2901585, dated Mar. 25, 2019, 42 pages.
Submission Document in Chilean Patent Application No. 2015-02311, dated Dec. 18, 2017, 40 pages (English Translation).
Submission Document in Chilean Patent Application No. 2015-02311, dated Jan. 8, 2016, 8 pages.
Submission Document in Chilean Patent Application No. 2015-02311, dated Jun. 13, 2017, 38 pages (English Translation).
Submission Document in Chinese Application No. 201580042132.3, dated Oct. 22, 2018, 15 pages (with English Translation).
Submission Document in Chinese Patent Application No. 201480009370.X, dated Feb. 25, 2016, 18 pages (English Translation).
Submission Document in Chinese Patent Application No. 201480009370.X, dated Mar. 21, 2017, 41 pages (English Translation).
Submission Document in Chinese Patent Application No. 201480009370.X, dated Oct. 10, 2016, 59 pages (English Translation).
Submission Document in Chinese Patent Application No. 201680007472.7, dated Oct. 10, 2019, 16 pages (with English Translation).
Submission Document in Chinese Patent Application No. 201680007472.7, dated Mar. 19, 2020, 8 pages (with English Translation).
Submission Document in Chinese Patent Application No. 201680068110.9, dated Oct. 8, 2018, 11 pages (English Translation).
Submission Document in Chinese Patent Application No. 201680068110.9, dated Jul. 8, 2020, 8 pages.
Submission Document in Egyptian Patent Application No. PCT1285/2015, dated Aug. 19, 2015, 2 pages (English Translation).
Submission Document in European Patent Application No. 14754294.8, dated Nov. 10, 2016, 9 pages.
Submission Document in European Patent Application No. 15834302.0, dated Oct. 2, 2018, 80 pages.
Submission Document in European Patent Application No. 15834302.0, dated Feb. 19, 2020, 74 pages.
Submission Document in European Patent Application No. 16768810.0, dated Feb. 11, 2019, 9 pages.
Submission Document in European Patent Application No. 18865416.4, dated Jul. 29, 2020, 11 pages.
Submission Document in Indian Patent Application No. 201747003469, dated Jan. 13, 2020, 12 pages.
Submission Document in Indian Patent Application No. 201747027065, dated May 21, 2020, 23 pages.
Submission Document in Indian Patent Application No. 4989/CHENP/2015, dated Apr. 15, 2019, 24 pages.
Submission Document in Indian Patent Application No. 4989/CHENP/2015, dated May 9, 2016, 7 pages (English Translation).
Submission Document in Indonesian Patent Application No. P-00201505035, dated Apr. 27, 2016, 10 pages (English Translation).
Submission Document in Indonesian Patent Application No. P-00201505035, dated Dec. 5, 2016, 3 pages.
Submission Document in Indonesian Patent Application No. P-00201505035, dated Apr. 26, 2019, 8 pages (with English Translation).
Submission Document in Israeli Patent Application No. 240623, dated Apr. 16, 2018, 15 pages (English Translation).
Submission Document in Israeli Patent Application No. 240623, dated May 18, 2016, 3 pages (English Translation).
Submission Document in Israeli Patent Application No. 250290, dated Dec. 26, 2018, 4 pages.
Submission Document in Israeli Patent Application No. 250290, dated Nov. 28, 2019, 8 pages (with English Translation).
Submission Document in Israeli Patent Application No. 253701, dated Feb. 4, 2019, 8 pages (English Translation).
Submission Document in Israeli Patent Application No. 253701, dated Feb. 5, 2020, 7 pages (with English Translation).
Submission Document in Israeli Patent Application No. 258671, dated Nov. 26, 2019, 4 pages (with English Translation).
Submission Document in Japanese Patent Application No. 2014-526292, dated May 30, 2014, 14 pages (English Translation).
Submission Document in Japanese Patent Application No. P2015-560425, dated Mar. 24, 2016, 8 pages (English Translation).
Submission Document in Japanese Patent Application No. P2017-508383, dated Feb. 8, 2019, 80 pages (English Translation).
Submission Document in Jordanian Patent Application No. 39/2014, dated Mar. 15, 2018, 12 pages (English Translation).
Submission Document in Korean Patent Application No. 10-2015-7022252, dated Oct. 25, 2019, 43 pages (with English Translation).
Submission Document in Malaysian Patent Application No. PI 2015702696, dated Apr. 7, 2016, 4 pages.
Submission Document in Malaysian Patent Application No. PI 2015702696, dated Jan. 6, 2016, 207 pages.
Submission Document in Mexican Patent Application No. MX/a/2015/010698, dated Aug. 2, 2018, 17 pages (English Translation).
Submission Document in Mexican Patent Application No. MX/a/2017/001624, dated Aug. 21, 2019, 11 pages (with English Translation).
Submission Document in New Zealand Patent Application No. 711101, dated Apr. 12, 2016, 9 pages.
Submission Document in New Zealand Patent Application No. 711101, dated Jan. 20, 2016, 5 pages.
Submission Document in New Zealand Patent Application No. 711101, dated Jul. 20, 2018, 6 pages.
Submission Document in Pakistani Patent Application No. 523/2016, dated Jun. 4, 2018, 1 page (English Translation).
Submission Document in Pakistani Patent Application No. 94/2014, dated Aug. 25, 2016, 14 pages.
Submission Document in Pakistani Patent Application No. 94/2014, dated Jul. 7, 2018, 4 pages.
Submission Document in Peruvian Patent Application No. 001748-2015, dated Dec. 21, 2015, 9 pages (English Translation).
Submission Document in Peruvian Patent Application No. 001748-2015, dated Jul. 6, 2019, 6 pages (with English Translation).
Submission Document in Peruvian Patent Application No. 001748-2015, dated Jun. 21, 2019, 4 pages (with English Translation).
Submission Document in Philippine Patent Application No. 1-2015-501813, dated Apr. 4, 2016, 1 page (English Translation).
Submission Document in Philippine Patent Application No. 1-2015-501813, dated Dec. 21, 2015, 3 pages (English Translation).
Submission Document in Russian Patent Application No. 2015134558, dated Apr. 22, 2016, 14 pages (English Translation).

(56) References Cited

OTHER PUBLICATIONS

Submission Document in Russian Patent Application No. 2015134558, dated Dec. 25, 2015, 16 pages.
Submission Document in Russian Patent Application No. 2015134558, dated Nov. 22, 2017, 21 pages (English Translation).
Submission Document in Russian Patent Application No. 2017103439, dated Mar. 20, 2018, 19 pages (English Translation).
Submission Document in Russian Patent Application No. 2017127135, dated Nov. 14, 2019, 21 pages (with English Translation).
Submission Document in Russian Patent Application No. 2018119102, dated Apr. 27, 2020, 14 pages (with English Translation).
Submission Document in Singaporean Patent Application No. 11201506488W, dated Dec. 23, 2015, 5 pages.
Submission Document in Singaporean Patent Application No. 11201700703X, dated Jul. 19, 2017, 16 pages (English Translation).
Submission Document in Singaporean Patent Application No. 11201706143S, dated May 30, 2019, 13 pages.
Submission Document in Sri Lankan Patent Application No. 18355, dated Nov. 21, 2019, 3 pages.
Submission Document in Taiwanese Patent Application No. 103105419, dated Aug. 8, 2018, 19 pages (English Translation).
Submission Document in Taiwanese Patent Application No. 103105419, dated Jan. 23, 2018, 30 pages (English Translation).
Submission Document in Thai Patent Application No. 1501004679, dated Jul. 20, 2018, 4 pages (English Translation).
Submission Document in Thai Patent Application No. 1501004679, dated Nov. 20, 2017, 6 pages (English Translation).
Submission Document in Ukrainian Patent Application No. a201508149, dated Nov. 20, 2017, 20 pages (English Translation).
Submission Document in Ukrainian Patent Application No. a201508149, dated Oct. 6, 2015, 4 pages (English Translation).
Submission Document in U.S. Appl. No. 15/547,139, dated Jul. 25, 2018, 13 pages.
Submission Document in U.S. Appl. No. 15/547,139, dated Dec. 17, 2018, 5 pages.
Submission Document in U.S. Appl. No. 15/547,139, dated Apr. 30, 2019, 11 pages.
Submission Document in U.S. Appl. No. 15/771,193, dated May 14, 2019, 8 pages.
Submission Document in U.S. Appl. No. 15/771,193, dated Aug. 22, 2019, 9 pages.
Submission Document in U.S. Appl. No. 15/771,193, dated Jan. 16, 2020, 20 pages.
Submission Document in U.S. Appl. No. 16/225,772, dated Dec. 19, 2018, 104 pages.
Submission Document in U.S. Appl. No. 16/225,772, dated Sep. 30, 2019, 10 pages.
Submission Document in U.S. Appl. No. 16/642,105, dated Jun. 8, 2020, 99 pages.
Submission Document in Vietnamese Patent Application No. 1-2015-02994, dated May 25, 2016, 12 pages (English Translation).
Submission Document in Vietnamese Patent Application No. 1-2015-02994, dated Oct. 28, 2015, 22 pages (English Translation).
Tsimafeyeu et al., "Overexpression of fibroblast growth factor receptors FGFR1 and FGFR2 in renal cell carcinoma", Scand J Urol Nephrol, 2011(45), p. 190-p. 195.
Tsuruoka et al., "Preclinical and clinical researches of lenvatinib mesylate (Lenvima capsule), a novel antitumor agent approved for thyroid cancer treatment," Folia Pharmacologica Japonica, 2015, 146:283-290 (with English Abstract).
Tsuruoka et al., "Preclinical and clinical researches of lenvatinib mesylate (Lenvima capsule), a novel anti tumor agent approved for thyroid cancer treatment," Folia Pharmacologica Japonica, 2015, 146:283-290 (with English Translation).
Turner et al., "FGFRI Amplification Drives Endocrine Therapy Resistance and Is a Therapeutic Target in Breast Cancer," Cancer Research, vol. 70, No. 5, Mar. 1, 2010, p. 2085-p. 2094.
Turner et al., "Fibroblast growth factor signaling: from development to cancer", Nature Reviews Cancer, 2010 vol. 10, p. 116-p. 129.

Watanabe et al., "Abstract 770: E7090: A potent and selective FGFR inhibitor with activity in multiple FGFR-driven cancer models with distinct mechanisms of activation," Cancer Research, 2015, 75(Suppl. 15):1-4, XP002792860 (Abstract Only).
Watanabe Miyano et al., "E7090, a Novel Selective Inhibitor of Fibroblast Growth Factor Receptors, Displays Potent Antitumor Activity and Prolongs Survival in Preclinical Models," Molecular Cancer Therapeutics, vol. 15, No. 11, Nov. 2016, p. 2630-p. 2639.
Weiss et al., "Frequent and Focal FGFR1 Amplification Associates with Therapeutically Tractable FGFR1 Dependency in Squamous Cell Lung Cancer", Sci Transl Med, Apr. 18, 2012, p. 1-p. 7.
Wesche et al., "Fibroblast growth factors and their receptors in cancer", Biochem J., 2011(437), p. 199-p. 213.
Wu et al., "Identification of Targetable FGFR Gene Fusions in Diverse Cancers," Cancer Discovery, 2013 American Association for Cancer, Research Brief, 2013, 13 pages.
Zhang et al., "Translating the Therapeutic Potential of AZD4547 in FGFR1-Amplified Non-Small Cell Lung Cancer through the Use of Patient-Derived Tumor Xenograft Models", Clinical Cancer Research, May 24, 2013, p. 6657-p. 6667.
Notice of Allowance in Brazilian Patent Application No. BR112015019790-6, dated Aug. 11, 2020, 2 pages (with English Translation).
Submission Document in Indian Patent Application No. 201747027065, dated Aug. 18, 2020, 6 pages.
International Preliminary Report on Patentability in International Application No. PCT/JP2019/012971, dated Oct. 8, 2020, 8 pages.
Notice of Allowance in European Patent Application No. 16875716.9, dated Oct. 28, 2020, 18 pages.
Notice of Allowance in Israeli Patent Application No. 253701, dated Nov. 11, 2020, 9 pages (with English Translation).
Notice of Allowance in Singaporean Patent Application No. 11201706143S, dated Oct. 29, 2020, 4 pages.
Notice of Allowance in U.S. Appl. No. 15/771,193, dated Oct. 22, 2020, 29 pages.
Office Action in Australian Patent Application No. 2016237222, dated Sep. 2, 2020, 6 pages.
Office Action in Israeli Patent Application No. 272887, dated Nov. 23, 2020, 5 pages (with English Translation).
Office Action in Japanese Application No. P2017-556119, dated Sep. 8, 2020, 6 pages (with English Translation).
Submission Document in Brazilian Patent Application No. BR1120170022680, dated Aug. 31, 2020, 21 pages (with English Translation).
Submission Document in Chinese Patent Application No. 201980013339.6, dated Oct. 23, 2020, 6 pages (with English Translation).
Submission Document in European Patent Application No. 16768810.0, dated Sep. 30, 2020, 5 pages.
Submission Document in Indian Patent Application No. 201847015401, dated Oct. 29, 2020, 20 pages.
Submission Document in Israeli Patent Application No. 258671, dated Sep. 30, 2020, 35 pages (with English Translation).
Submission Document in Mexican Patent Application No. MX/a/2018/006329, dated Oct. 8, 2020, 7 pages (with English Translation).
Submission Document in U.S. Appl. No. 16/225,772, dated Oct. 21, 2020, 5 pages.
Office Action in Chinese Patent Application No. 201680068110.9, dated Nov. 24, 2020, 9 pages (with English Translation).
Notice of Allowance in European Patent Application No. 16768810.0, dated Mar. 16, 2021, 71 pages.
Notice of Allowance in Japanese Patent Application No. P2017-556119, dated Mar. 16, 2021, 6 pages (with English Translation).
Notice of Allowance in Mexican Patent Application No. MX/a/2017/009892, dated Dec. 15, 2020, 6 pages (with English Translation).
Notice of Allowance in U.S. Appl. No. 15/547,139, dated Feb. 5, 2021, 23 pages.
Notice of Allowance in U.S. Appl. No. 15/771,193, dated Feb. 4, 2021, Feb. 4, 2021, 15 pages.
Notice of Allowance in U.S. Appl. No. 16/225,772, dated Mar. 29, 2021, 22 pages.

(56) References Cited

OTHER PUBLICATIONS

Office Action in Argentine Patent Application No. P140100495, dated Jan. 22, 2021, 10 pages (with English Translation).
Office Action in Australian Patent Application No. 2016237222, dated Jan. 29, 2021, 4 pages.
Office Action in Brazilian Patent Application No. BR1120170163926, dated Dec. 8, 2020, 10 pages (with English Translation).
Office Action in Brazilian Patent Application No. BR1120180101036, dated Feb. 9, 2021, 9 pages (with English Translation).
Office Action in Indian Patent Application No. 201747003469, dated Jan. 8, 2021, 2 pages (with English Translation).
Office Action in Mexican Patent Application No. MX/a/2018/006329, dated Jan. 19, 2021, 8 pages (with English Translation).
Submission Document in Australian Patent Application No. 2016237222, dated Jan. 19, 2021, 20 pages.
Submission Document in Australian Patent Application No. 2016237222, dated Mar. 22, 2021, 10 pages.
Submission Document in Brazilian Patent Application No. BR1120170163 926, dated Mar. 5, 2021, 19 pages (with English Translation).
Submission Document in Chinese Patent Application No. 201680068110.9, dated Mar. 1, 2021, 14 pages (with English Translation).
Submission Document in Indian Patent Application No. 201747003469, dated Feb. 9, 2021, 8 pages.
Submission Document in Israeli Patent Application No. 272887, dated Mar. 16, 2021, 7 pages (with English Translation).
Submission Document in Mexican Patent Application No. MX/a/2018/006329, dated Mar. 11, 2021, 9 pages (with English Translation).
Submission Document in U.S. Appl. No. 15/771,193, dated Jan. 21, 2021, 12 pages.
Notice of Allowance in U.S. Appl. No. 16/225,772, dated Jul. 12, 2021, 14 pages.
[No Author], "Guidance for Industry—Estimating the Maximum Safe Starting Dose in Initial Clinical Trials for Therapeutics in Adult Healthy Volunteers," U.S. Department of Health and Human Services, Food and Drug Administration, Center for Drug Evaluation and Research (CDER), Pharmacology and Toxicology, Jul. 2005, 30 pages.
European Search Report in European Application No. 18865416.4, dated May 28, 2021, 9 pages.
Koyama et al., "Abstract B160: First-in-human phase 1 study of E7090, a novel selective inhibitor of FGFRs, in patients with advanced solid tumors," Abstract, AACR-NCI-EORTC International Conference: Molecular Targets and Cancer Therapeutics, Jan. 2018, [Retrieved on May 18, 2021], retrieved from: URL<https://mct.aacjournals.org/content/17/1_Supplement/B160>, 4 pages.
Notice of Allowance in Malaysian Patent Application No. PI2015702696, dated Jul. 9, 2020, 2 pages (with English Translation).
Notice of Allowance in U.S. Appl. No. 15/547,139, dated May 12, 2021, 12 pages.
Notice of Allowance in U.S. Appl. No. 15/771,193, dated May 11, 2021, 12 pages.
Office Action in Australian Patent Application No. 2016374441, dated May 31, 2021, 4 pages.
Office Action in Canadian Patent Application No. 2956270, dated Apr. 22, 2021, 4 pages.
Office Action in European Patent Application No. 15834302.0, dated May 14, 2021, 4 pages.
Office Action in Indian Patent Application No. 201847015401, dated Jun. 29, 2021, 3 pages (with English Translation).
Office Action in Israeli Patent Application No. 258671, dated May 10, 2021, 18 pages (with English Translation).
Office Action in Israeli Patent Application No. 276935, dated Apr. 22, 2021, 5 pages (with English Translation).
Office Action in Mexican Patent Application No. MX/a/2018/006329, dated May 14, 2021, 5 pages (with English Translation).
Office Action in U.S. Appl. No. 16/642,105, dated Jun. 28, 2021, 65 pages.
Submission Document in Brazilian Patent Application No. BR1120180101036, dated Apr. 26, 2021, 20 pages (with English Translation).
Submission Document in U.S. Appl. No. 15/771,193, dated May 3, 2021, 5 pages.
Notice of Allowance in Australian Patent Application No. 2016237222, dated Apr. 16, 2021, 4 pages.
Submission Document in Israeli Patent Application No. 276935, dated Jul. 13, 2021, 4 pages (with English Translation).
Formisano et al., "Association of FGFR1 with ERα Maintains Ligand-Independent ER Transcription and Mediates Resistance to Estrogen Deprivation in ER+ Breast Cancer," Clinical Cancer Research, 2017, 23(20):6138-6150.
International Search Report and Written Opinion in International Application No. PCT/JP2021/028008, dated Aug. 31, 2021 21 pages (with English Translation).
Katoh, "Fibroblast growth factor receptors as treatment targets in clinical oncology," Nature Reviews, Clinical Oncology, 2019, 16(2):105-122.
Musolino et al., "Phase II, randomized, placebo-controlled study of dovitinib in combination with fulvestrant in postmenopausal patients with HR+, HER2—breast cancer that had progressed during or after prior endocrine therapy," Breast Cancer Research, 2017, 19:18.
Notice of Allowance in Australian Patent Application No. 2016374441, dated Oct. 8, 2021, 3 pages.
Notice of Allowance in U.S. Appl. No. 15/547,139, dated Oct. 4, 2021, 24 pages.
Notice of Allowance in U.S. Appl. No. 15/547,139, dated Oct. 20, 2021, 12 pages.
Notice of Allowance in U.S. Appl. No. 15/771,193, dated Aug. 27, 2021, 26 pages.
Notice of Allowance in U.S. Appl. No. 16/225,772, dated Jul. 23, 2021, 10 pages.
Office Action in Brazilian Patent Application No. BR1120170022680, dated Apr. 7, 2020, 9 pages (with English Translation).
Office Action in Canadian Patent Application No. 2956270, dated Sep. 28, 2021, 3 pages.
Office Action in Chinese Patent Application No. 201680007472.7, dated Aug. 9, 2021, 10 pages (with English Translation).
Office Action in Korean Patent Application No. 10-2017-7002791, dated Aug. 29, 2021, 7 pages (with English Translation).
Quintela-Fandino et al., "Nintedanib plus letrozole in early breast cancer: a phase 0/1 pharmacodynamic, pharmacokinetic, and safety clinical trial of combined FGFR1 and aromatase inhibition," Breast Cancer Research, 2019, 21:69.
Seckl et al., "Radical trial: A phase Ib/IIa study to assess the safety and efficacy of AZD4547 in combination with either anastrozole or letrozole in ER positive breast cancer patients progressing on these aromatase inhibitors (AIs)," Journal of Clinical Oncology, 2017, 35(15):Supplement 1, 4 pages.
Submission Document in Australian Patent Application No. 2016374441, dated Sep. 22, 2021, 9 pages.
Submission Document in Brazilian Patent Application No. BRI 120200038490, dated Sep. 9, 2021, 51 pages (with English Translation).
Submission Document in Canadian Patent Application No. 2956270, dated Jun. 22, 2021, 26 pages.
Submission Document in European Patent Application No. 15834302.0, dated Sep. 14, 2021, 75 pages.
Submission Document in Indian Patent Application No. 201847015401, dated Aug. 11, 2021, 6 pages.
Submission Document in Israeli Patent Application No. 258671, dated Aug. 3, 2021, 4 pages (with English Translation).
Submission Document in Korean Patent Application No. 10-2017-7002791, dated Oct. 8, 2021, 23 pages (with English Translation).
Submission Document in Korean Patent Application No. 10-2020-7005278, dated Jul. 29, 2021, 12 pages (with English Translation).
Submission Document in U.S. Appl. No. 15/771,193, dated Aug. 9, 2021, 5 pages.
Submission Document in U.S. Appl. No. 16/642,105, dated Sep. 15, 2021, 7 pages.

(56) References Cited

OTHER PUBLICATIONS

Notice of Allowance in European Patent Application No. 15834302.0, dated Oct. 21, 2021, 56 pages.
Office Action in U.S. Appl. No. 16/642,105, dated Oct. 18, 2021, 19 pages.
Submission Document in Canadian Patent Application No. 2956270, dated Oct. 25, 2021, 7 pages.

* cited by examiner

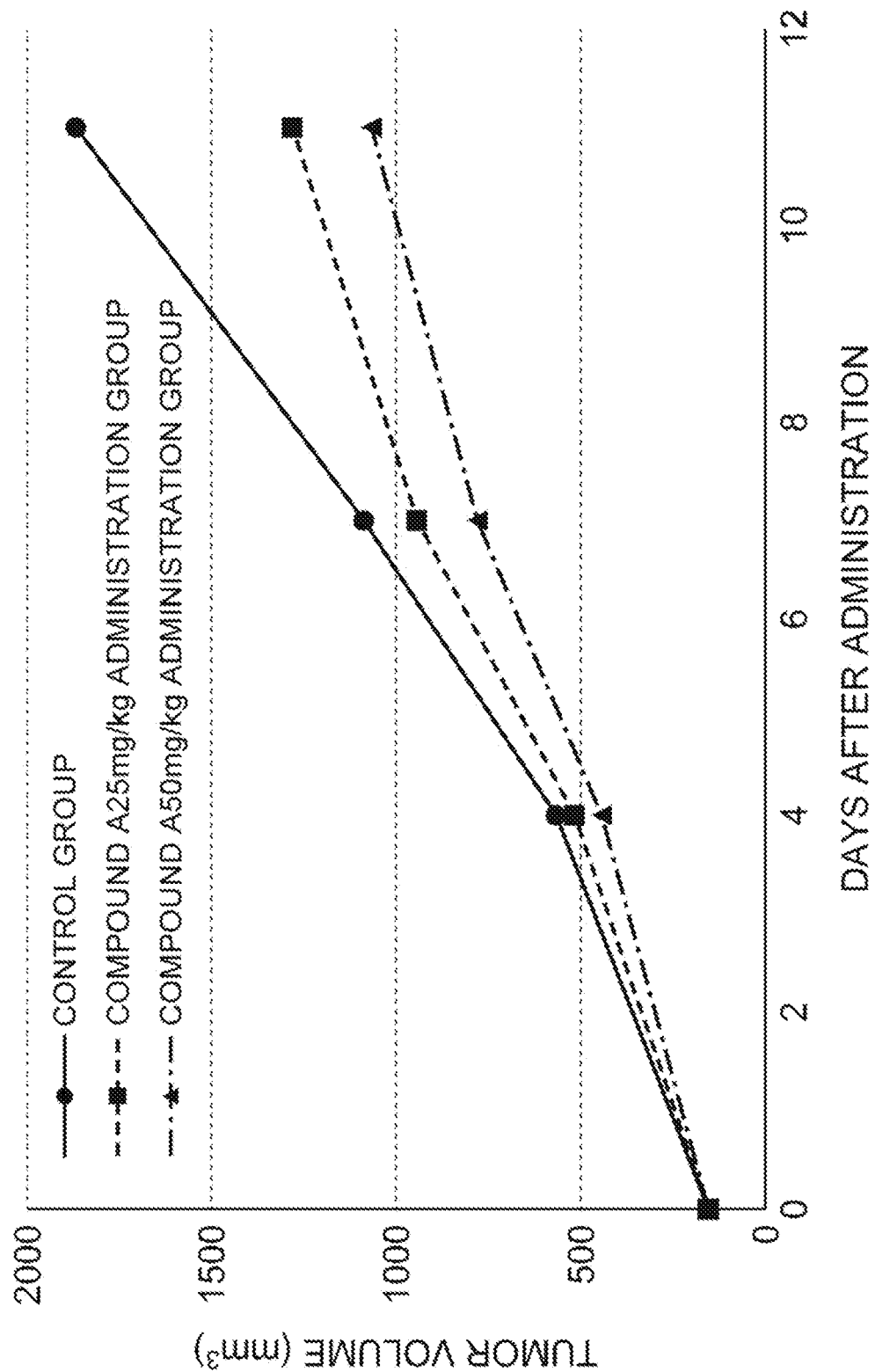

THERAPEUTIC AGENT FOR HEPATOCELLULAR CARCINOMA

TECHNICAL FIELD

The present invention relates to a therapeutic agent for hepatocellular carcinoma, comprising a monocyclic pyridine derivative having a fibroblast growth factor receptor (FGFR) inhibitory action or a pharmacologically acceptable salt thereof. More specifically, the present invention relates to a therapeutic agent for hepatocellular carcinoma, comprising 5-((2-(4-(1-(2-hydroxyethyl)piperidin-4-yl)benzamide)pyridin-4-yl)oxy)-6-(2-methoxyethoxy)-N-methyl-1H-indole-1-carboxamide or a pharmacologically acceptable salt thereof.

BACKGROUND ART

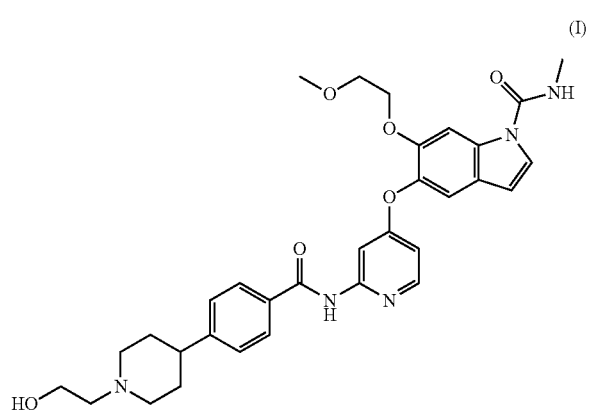 [SMILES: CNC(=O)n1ccc2cc(Oc3ccnc(NC(=O)c4ccc(C5CCN(CCO)CC5)cc4)c3)c(OCCOC)cc21]

(I)

It has been reported that 5-((2-(4-(1-(2-hydroxyethyl)piperidin-4-yl)benzamide)pyridin-4-yl)oxy)-6-(2-methoxyethoxy)-N-methyl-1H-indole-1-carboxamide represented by formula (I) is known as an inhibitor against FGFR1, FGFR2 or FGFR3, and has an inhibitory action on the cell proliferation of stomach cancer, lung cancer, bladder cancer, and endometrial cancer (Patent Literature 1). It has been reported that the above compound exerts a high therapeutic effect against bile duct cancer (Patent Literature 2) and breast cancer (Patent Literature 3). As the pharmacologically acceptable salt of the above compound, a succinate and a maleate are known (Patent Literature 4).

Hepatocellular carcinoma develops due to malignant transformation of liver cells following chronic hepatitis or liver cirrhosis. Examples of the causes of the development of hepatocellular carcinoma include excessive alcohol intake, excessive calorie intake, viral infection, and genetic predisposition.

Examples of the methods for treating hepatocellular carcinoma include surgical resection, cautery, hepatic artery embolization, and ethanol injection therapy. However, these treatment methods are limited to the use in a case where the area of development of hepatocellular carcinoma is narrow. In a case where many cancer foci are recognized, or in a case where many cancer foci are spread to other organs, chemotherapy is performed by transhepatic arterial infusion or systemic administration of an antitumor agent. As the drugs effective in the treatment of hepatocellular carcinoma, regorafenib, sorafenib (Non Patent Literatures 1 and 2) and the like are known, but such drugs often cause adverse drug reactions such as pneumonia, hypertension, and hand-foot syndrome, and therefore, further, the development of a novel drug is awaited.

CITATION LIST

Patent Literature

Patent Literature 1: US 2014-0235614 A
Patent Literature 2: US 2018-0015079 A
Patent Literature 3: International Publication No. WO 2017/104739
Patent Literature 4: US 2017-0217935 A

Non Patent Literature

Non Patent Literature 1: Kim K. et al., Regorafenib in advanced hepatocellular carcinoma (HCC): considerations for treatment, Cancer Chemotherapy and Pharmacology, 80, 945-954, 2017
Non Patent Literature 2: Josep M. et al., Sorafenib in Advanced Hepatocellular Carcinoma, The New England Journal of Medicine, 359, 378-390, 2008

SUMMARY OF INVENTION

Technical Problem

An object of the present invention is to provide a novel therapeutic agent for hepatocellular carcinoma.

Solution to Problem

In view of the above circumstances, as a result of intensive studies, the present inventors have found that the compound represented by the above formula (I) exerts a high therapeutic effect against hepatocellular carcinoma, and thus have completed the present invention.

That is, the present invention provides the following [1] to [10].

[1] A therapeutic agent for hepatocellular carcinoma, comprising a compound represented by formula (I) or a pharmacologically acceptable salt thereof:

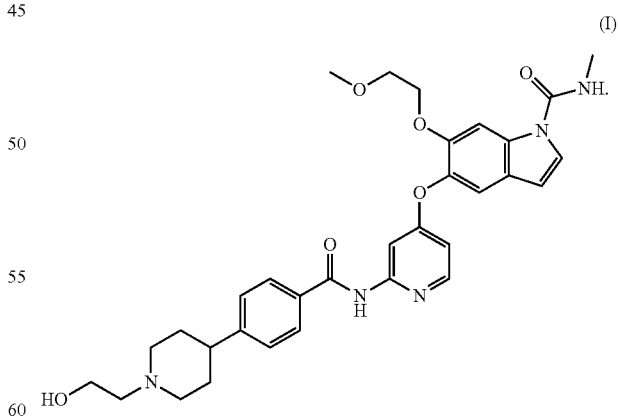

(I)

[2] Use of a compound represented by formula (I) or a pharmacologically acceptable salt thereof, for treatment of hepatocellular carcinoma.
[3] A compound represented by formula (I) or a pharmacologically acceptable salt thereof, for use in treatment of hepatocellular carcinoma.

[4] A method for treating hepatocellular carcinoma, comprising administering a compound represented by formula (I) or a pharmacologically acceptable salt thereof to a patient in need thereof.

[5] A composition for treating hepatocellular carcinoma, comprising a compound represented by formula (I) or a pharmacologically acceptable salt thereof.

[6] A composition for treating hepatocellular carcinoma, comprising a compound represented by formula (I) or a pharmacologically acceptable salt thereof, and an excipient.

[7] The therapeutic agent, use, compound, method, or composition as above, wherein the hepatocellular carcinoma is metastatic hepatocellular carcinoma or recurrent hepatocellular carcinoma.

[8] The therapeutic agent, use, compound, method, or composition as above, wherein the hepatocellular carcinoma expresses an FGFR.

[9] The therapeutic agent, use, compound, method, or composition as above, wherein the FGFR is FGFR1, FGFR2, or FGFR3.

[10] The therapeutic agent, use, compound, method, or composition as above, wherein the pharmacologically acceptable salt of the compound represented by formula (I) is a sesquisuccinate.

Advantageous Effects of Invention

The compound represented by formula (I) may exert an effect of reducing a tumor volume against hepatocellular carcinoma.

BRIEF DESCRIPTION OF DRAWINGS

The FIGURE is a graph showing the results of Example 4. The ordinate shows the tumor volume, and the abscissa shows the days after administration.

DESCRIPTION OF EMBODIMENTS

The compound represented by formula (I) or a pharmacologically acceptable salt thereof according to the present invention can be produced by the method disclosed in Patent Literature 1.

In the present specification, examples of the pharmacologically acceptable salt include a salt with an inorganic acid, a salt with an organic acid, and a salt with an acidic amino acid.

Preferable examples of the salt with an inorganic acid include salts with hydrochloric acid, hydrobromic acid, sulfuric acid, nitric acid, and phosphoric acid.

Preferable examples of the salt with an organic acid include salts with acetic acid, succinic acid, fumaric acid, maleic acid, tartaric acid, citric acid, lactic acid, stearic acid, benzoic acid, methanesulfonic acid, ethanesulfonic acid, and p-toluenesulfonic acid.

Preferable examples of the salt with an acidic amino acid include salts with aspartic acid and glutamic acid.

A preferable pharmacologically acceptable salt is a succinate or a maleate, and a more preferable salt is a succinate. In particular, it is preferable for the salt to be a sesquisuccinate.

The therapeutic agent for hepatocellular carcinoma according to the present invention can be administered orally in a form of a solid preparation such as a tablet, granules, fine particles, powder, or a capsule, a liquid, a jelly, a syrup, or the like. Further, the therapeutic agent for hepatocellular carcinoma according to the present invention may be administered parenterally in a form of an injection, a suppository, ointment, a cataplasm, or the like.

The therapeutic agent for hepatocellular carcinoma according to the present invention can be formulated by the method described in The Japanese Pharmacopoeia, Seventeenth Edition.

The dose of a compound represented by formula (I) or a pharmacologically acceptable salt thereof can be appropriately selected depending on the severity of symptoms, the age, sex, body weight, and differential sensitivity of a patient, the route of administration, the time of administration, the intervals of administration, the type of pharmaceutical preparation, and the like. In general, in a case of oral administration to an adult (body weight: 60 kg), the dose is 100 µg to 10 g, preferably 500 µg to 10 g, and furthermore preferably 1 mg to 5 g, per day. This dose may be administered in 1 to 3 divided portions per day.

In the present specification, the hepatocellular carcinoma means a benign or malignant tumor developed in the liver cells. The hepatocellular carcinoma includes metastatic hepatocellular carcinoma in an organ tissue other than the liver, or recurrent hepatocellular carcinoma.

EXAMPLES

Hereinafter, the present invention is further described in detail by referring to Examples.

Production Example 1

By the method disclosed in the specification of US 2017-0217935 A, 5-((2-(4-(1-(2-hydroxyethyl)piperidin-4-yl)benzamide)pyridin-4-yl)oxy)-6-(2-methoxyethoxy)-N-methyl-1H-indole-1-carboxamide sesquisuccinate (hereinafter, referred to as compound A) was produced.

Example 1: $IC_{50}$ of Compound A Against Proliferation of Hepatocellular Carcinoma Cell Line As the human hepatocellular carcinoma cell line, SNU-398, Li-7, Hep3B2.1-7, and HuH-7 were used. In this regard, SNU-398, and Hep3B2.1-7 were obtained from American Type Culture Collection (ATCC), Li-7 was obtained from Cell Resource Center for Biomedical Research, Institute of Development, Aging and Cancer, Tohoku University, and HuH-7 was obtained from JCRB Cell Bank, respectively.

For each cell line, maintenance culture was performed by using the following medium.
(1) SNU-398 and Li-7
An RPMI-1640 medium (Wako Pure Chemical Industries, Ltd.) containing 10% fetal bovine serum (FBS) and penicillin/streptomycin
(2) HuH-7
A DMEM-low glucose medium (Wako Pure Chemical Industries, Ltd.) containing 10% FBS and penicillin/streptomycin
(3) Hep3B2.1-7
An EMEM medium (Wako Pure Chemical Industries, Ltd.) containing 10% FBS and penicillin/streptomycin Into each well of a 96-well clear-bottom black plate (Corning Incorporated, catalog number: 3904), a suspension of each cell, which had been prepared to be 0.75 to $1.25 \times 10^4$ cells-mL, was added in an amount of 80 to 90 µL, and the cells were cultured overnight in a 5% $CO_2$ incubator (37° C.). To the obtained cultured cells, a compound A diluted in each medium containing 10% FBS was added in an amount of 10 to 20 μL so that the mixture to be obtained was adjusted to be in a liquid amount of 100 μL, and then the obtained mixture was cultured for 6 days in a 5% $CO_2$ incubator (37° C.).

The number of cells in each well after the culture was calculated by measuring the intracellular ATP level with the emission intensity using CellTiter Glo-2.0 (Promega Corporation, catalog number: G9243).

CellTiter Glo-2.0 was added in an amount of 50 μL into each well, and the mixture was mixed for 10 minutes with a plate mixer. After that, the mixture was allowed to react at room temperature for 10 minutes, and then the luminescence was measured with Multilabel Reader (ARVO X4, PerkinElmer, Inc.) The luminescence value ratio in the presence of a compound A was determined, assuming that the luminescence value in a case where Compound A had not added was set to 100% and the luminescence value in a well where cells had not been present was set to 0%. The concentration required for inhibiting the cell proliferation by 50% ($IC_{50}$ value) of the test substance was calculated. The results are shown in Table 1.

TABLE 1

| Name of cell | $IC_{50}$ (nmol/L) |
|---|---|
| SNU-398 | 26 |
| Hep3B2.1-7 | 77 |
| HuH-7 | 249 |
| Li-7 | 63 |

Example 2: Antitumor Action of Compound A Against Human Hepatocellular Carcinoma Cell Line (HuH-7)

Five nude mice (CAnN.Cg-Foxn1nu/CrlCrlj, female, CHARLES RIVER LABORATORIES JAPAN, INC.) were used in each group, and the antitumor effect in a case where compound A was administered was evaluated.

Human-derived hepatocellular carcinoma cell line HuH-7 (obtained from JCRB Cell Bank) cells were suspended in a DMEM medium (Wako Pure Chemical Industries, Ltd.) containing 10% bovine serum so that the concentration of the cells was $8.0 \times 10^7$ cells/mL. Into the suspension, Matrigel™ Matrix (Becton, Dickinson and Company, Japan) in the same volume as that of the suspension was added, and the obtained mixture was sufficiently mixed. The mixture in an amount of 0.1 mL was transplanted into the subcutaneous part in the right flank of each mouse, and the mouse was subjected to the antitumor effect evaluation.

On 11 days after the transplantation, the longest diameter and the short axis of the tumor were measured with an electronic digital caliper (Digimatic™ Caliper, Mitutoyo Corporation). The mice were divided into groups so that the average values of the tumor volumes in the respective groups were nearly equal to each other. In addition, the tumor volume was calculated in accordance with the following equation.

Tumor volume ($mm^3$)=longest diameter (mm)×short axis (mm)×short axis (mm)/2

Compound A was dissolved in purified water so that the concentration of compound A was 2.5 mg/mL.

Compound A was administered to each of the mice in the respective groups at a dose of 50 mg/kg once daily for 5 days. After that, compound A was withdrawn for 2 days, and then administered orally for 3 days. In this regard, the volume to be administered was set to 20 mL/kg, and to the control group, purified water in the same volume was administered.

The measured values of the tumor volumes in the control group and the compound A administration group are shown in Table 2.

TABLE 2

| Measurement date | Day 0 | Day 3 | Day 7 | Day 10 |
|---|---|---|---|---|
| Control group ($mm^3$) | 147.3 | 500.7 | 1168.7 | 1767.0 |
| Compound A group ($mm^3$) | 148.1 | 409.2 | 939.9 | 1400.9 |

Example 3: Antitumor Action of Compound A Against Human Hepatocellular Carcinoma Cell Line (Hep3B2.1-7)

Five nude mice (CAnN.Cg-Foxn1nu/CrlCrlj, female, CHARLES RIVER LABORATORIES JAPAN, INC.) were used in each group, and the antitumor effect in a case where compound A was administered was evaluated.

Human-derived hepatocellular carcinoma cell line Hep3B2.1-7 (obtained from ATCC) cells were suspended in a Hank's Balanced Salt Solution (HBSS) so that the concentration of the cells was $4 \times 10^7$ cells/mL. Into the suspension, Matrigel™ Matrix (Becton, Dickinson and Company, Japan) in the same volume as that of the suspension was added, and the obtained mixture was sufficiently mixed. The mixture in an amount of 0.1 mL was transplanted into the subcutaneous part in the right flank of each mouse, and the mouse was subjected to the antitumor effect evaluation.

On 19 days after the transplantation, the longest diameter and the short axis of the tumor were measured with an electronic digital caliper (Digimatic™ Caliper, Mitutoyo Corporation). The mice were divided into groups so that the average values of the tumor volumes in the respective groups were substantially equal to each other. In addition, the tumor volume was calculated in accordance with the following equation.

Tumor volume ($mm^3$)=longest diameter (mm)×short axis (mm)×short axis (mm)/2

Compound A was dissolved in purified water so that the concentration of compound A was 5 mg/mL.

Compound A was administered to each of the mice in the respective groups at a dose of 100 mg/kg once daily for 5 days. After that, compound A was withdrawn for 2 days, and then administered orally for 4 days. In this regard, the volume to be administered was set to 20 mL/kg, and to the control group, purified water in the same volume was administered.

The measured values of the tumor volumes in the control group and the compound A administration group are shown in Table 3.

TABLE 3

| Measurement date | Day 0 | Day 3 | Day 7 | Day 11 |
|---|---|---|---|---|
| Control group ($mm^3$) | 411.9 | 645.5 | 811.7 | 1040.0 |
| Compound A group ($mm^3$) | 417.4 | 504.0 | 630.4 | 862.3 |

Example 4: Antitumor Action of Compound A Against Human Hepatocellular Carcinoma Cell Line (SNU-398)

Five nude mice (CAnN.Cg-Foxn1nu/CrlCrlj, female, CHARLES RIVER LABORATORIES JAPAN, INC.) were used in each group, and the antitumor effect in a case where compound A was administered was evaluated.

Human-derived hepatocellular carcinoma cell line SNU-398 (obtained from ATCC) cells were suspended in a HBSS so that the concentration of the cells was $5 \times 10^7$ cells/mL. Into the suspension, Matrigel™ Matrix (Becton, Dickinson and Company, Japan) in the same volume as that of the suspension was added, and the obtained mixture was sufficiently mixed. The mixture in an amount of 0.1 mL was transplanted into the subcutaneous part in the right flank of each mouse, and the mouse was subjected to the antitumor effect evaluation.

On 9 days after the transplantation, the longest diameter and the short axis of the tumor were measured with an electronic digital caliper (Digimatic™ Caliper, Mitutoyo Corporation). The mice were divided into groups so that the average values of the tumor volumes in the respective groups were nearly equal to each other. In addition, the tumor volume was calculated in accordance with the following equation.

Tumor volume (mm³)=longest diameter (mm)×short axis (mm)×short axis (mm)/2

Compound A was dissolved in purified water so that the concentration of compound A was 1.25 mg/kg or 2.5 mg/mL.

Compound A was administered orally to each of the mice in the respective groups at a dose of 25 mg/kg or 50 mg/kg once daily for 11 days. In this regard, the volume to be administered was set to 20 mL/kg. The control group was untreated.

The measured values of the tumor volumes in the control group and compound A administration group are shown in Table 4 and The FIGURE. The increase in the tumor volume was suppressed in a dose-dependent manner by the administration of compound A.

TABLE 4

| Measurement date | Day 0 | Day 4 | Day 7 | Day 11 |
|---|---|---|---|---|
| Control group (mm³) | 154.5 | 566.0 | 1086.9 | 1868.0 |
| Compound A at 25 mg/kg group (mm³) | 154.5 | 516.4 | 942.2 | 1280.1 |
| Compound A at 50 mg/kg group (mm³) | 153.9 | 443.2 | 779.0 | 1066.1 |

The invention claimed is:

1. A method for treating hepatocellular carcinoma, comprising administering a compound represented by formula (I) or a pharmacologically acceptable salt thereof:

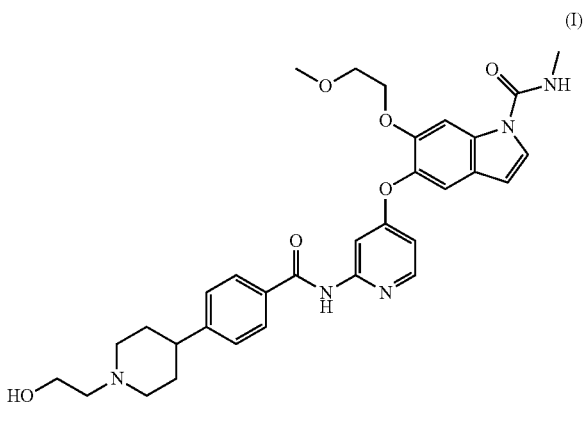 [SMILES: CNC(=O)n1ccc2cc(Oc3ccnc(NC(=O)c4ccc(C5CCN(CCO)CC5)cc4)c3)c(OCCOC)cc21]

(I)

to a patient in need thereof.

2. The method according to claim 1, wherein the salt is a sesquisuccinate.

* * * * *

UNITED STATES PATENT AND TRADEMARK OFFICE
CERTIFICATE OF CORRECTION

Page 1 of 1

PATENT NO. : 11,219,619 B2
APPLICATION NO. : 16/970683
DATED : January 11, 2022
INVENTOR(S) : Atsumi Yamaguchi et al.

It is certified that error appears in the above-identified patent and that said Letters Patent is hereby corrected as shown below:

On the Title Page

Column 2, Item (57) Abstract:
Line 2, delete "(4-(2-" and insert -- (4-(1-(2- --.

Signed and Sealed this
Seventh Day of June, 2022

Katherine Kelly Vidal
*Director of the United States Patent and Trademark Office*